(12) United States Patent
Ruiz-Vela

(10) Patent No.: US 10,182,885 B2
(45) Date of Patent: Jan. 22, 2019

(54) SELF-LIGATING BRACKET

(71) Applicant: MEM DENTAL TECHNOLOGY CO., LTD., Tainan (TW)

(72) Inventor: Alberto Ruiz-Vela, Alta Loma, CA (US)

(73) Assignee: MEM DENTAL TECHNOLOGY CO., LTD (TW)

( * ) Notice: Subject to any disclaimer, the term of this patent is extended or adjusted under 35 U.S.C. 154(b) by 0 days.

(21) Appl. No.: 14/926,815

(22) Filed: Oct. 29, 2015

(65) Prior Publication Data

US 2017/0119500 A1    May 4, 2017

(51) Int. Cl.
*A61C 7/30*    (2006.01)
*A61C 7/28*    (2006.01)

(52) U.S. Cl.
CPC .............. *A61C 7/287* (2013.01); *A61C 7/30* (2013.01)

(58) Field of Classification Search
CPC .. A61C 7/12; A61C 7/14; A61C 7/143; A61C 7/148; A61C 7/20; A61C 7/28; A61C 7/287; A61C 7/16; A61C 7/141; A61C 7/145; A61C 7/22; A61C 7/30; A61C 7/34
USPC ........................................ 433/8–12
See application file for complete search history.

(56) References Cited

U.S. PATENT DOCUMENTS

| | | | |
|---|---|---|---|
| 2,381,128 A | 8/1945 | Laskin | |
| 3,854,207 A | 12/1974 | Wildman | |
| 4,676,746 A | 6/1987 | Klapper | |
| 5,322,435 A | 6/1994 | Pletcher | |
| 5,466,151 A | 11/1995 | Damon | |
| 6,071,118 A | 6/2000 | Damon | |
| 6,726,474 B2 | 4/2004 | Spencer | |
| 7,134,873 B2 | 11/2006 | Miyaji et al. | |
| 7,419,375 B2 | 9/2008 | Farzin-Nia et al. | |
| 7,585,171 B2 | 9/2009 | Hagelganz | |
| 7,621,743 B2 | 11/2009 | Bathen et al. | |
| 7,785,101 B2 | 8/2010 | Förster | |
| 7,963,767 B2 | 6/2011 | Lewis et al. | |

(Continued)

FOREIGN PATENT DOCUMENTS

CN    201617965 U    11/2010
CN    102670314 A    6/2012

(Continued)

OTHER PUBLICATIONS

International Search Report dated Feb. 27, 2014 issued in corresponding PCT/IB2013-060064.

(Continued)

*Primary Examiner* — Edward Moran
*Assistant Examiner* — Drew Folgmann
(74) *Attorney, Agent, or Firm* — Vedder Price P.C.

(57) ABSTRACT

An orthodontic bracket includes a bracket body with a recess on a top surface of the bracket body and an archwire slot adapted to receive an orthodontic wire. The orthodontic bracket also includes a ligating member with a projection on its bottom surface. The ligating member is movably connected to the bracket body for retaining the orthodontic wire in the archwire slot when the ligating member is moved from an open position to a closed position. The orthodontic bracket also includes a discrete spring positioned in the recess on the bracket body such that a force is required to move the ligating member from the open position to the closed position.

6 Claims, 12 Drawing Sheets

(56) References Cited

U.S. PATENT DOCUMENTS

| | | | |
|---|---|---|---|
| 7,967,603 B2 | 6/2011 | Heiser | |
| 8,029,275 B2 | 10/2011 | Kesling | |
| D648,030 S | 11/2011 | Bryant et al. | |
| 8,469,704 B2 | 6/2013 | Oda et al. | |
| 8,979,528 B2 | 3/2015 | Macchi et al. | |
| 2004/0072117 A1 | 4/2004 | Farzin-Nia et al. | |
| 2007/0248928 A1 | 10/2007 | Damon | |
| 2008/0070184 A1 | 3/2008 | Farzin-Nia et al. | |
| 2008/0113311 A1 | 5/2008 | Forster | |
| 2010/0178629 A1 | 7/2010 | Oda et al. | |
| 2010/0196838 A1 | 8/2010 | Damon | |
| 2010/0285420 A1* | 11/2010 | Oda | A61C 7/287 433/11 |
| 2011/0047799 A1 | 3/2011 | Abels et al. | |
| 2012/0135364 A1 | 5/2012 | Tunebert et al. | |
| 2013/0236847 A1 | 9/2013 | Shin | |
| 2014/0134562 A1* | 5/2014 | Wu | A61C 7/287 433/11 |

FOREIGN PATENT DOCUMENTS

| | | |
|---|---|---|
| CN | 102688104 A | 6/2012 |
| DE | 102006053215 A1 | 5/2008 |
| DE | 202009014055 U1 | 2/2010 |
| DE | 202009015708 U1 | 4/2010 |
| DE | 102009049659 A1 | 4/2011 |
| EP | 0623320 A1 | 11/1994 |
| EP | 0 944 365 | 9/1999 |
| EP | 1 063 936 | 1/2001 |
| EP | 2 269 537 A2 | 1/2001 |
| EP | 1 508 310 A2 | 2/2005 |
| EP | 1 679 048 A2 | 7/2006 |
| EP | 1 723 926 A2 | 11/2006 |
| EP | 1 723 927 A1 | 11/2006 |
| EP | 2 008 611 A1 | 12/2008 |
| EP | 2 124 807 | 12/2009 |
| EP | 2 170 210 | 4/2010 |
| EP | 2 228 031 A1 | 9/2010 |
| EP | 2 266 495 A1 | 12/2010 |
| EP | 2 266 496 A1 | 12/2010 |
| EP | 2 349 063 | 8/2011 |
| EP | 2 381 880 | 11/2011 |
| EP | 2 387 370 | 11/2011 |
| EP | 2 6030 932 A1 | 8/2013 |
| EP | 2 644 150 A1 | 10/2013 |
| EP | 2 671535 A1 | 12/2013 |
| EP | 2 730 250 A1 | 5/2014 |
| EP | 2 777 599 A1 | 9/2014 |
| EP | 2 783 656 A1 | 10/2014 |
| ES | 1073326 Y | 12/2010 |
| FR | 2 974 293 | 10/2012 |
| WO | WO 2009/015157 A1 | 1/2009 |
| WO | WO 2009/057937 A2 | 5/2009 |
| WO | WO 2009/098714 A2 | 8/2009 |
| WO | 2010-019768 A1 | 2/2010 |
| WO | WO 2010/105430 A1 | 9/2010 |
| WO | WO 2011/118455 A1 | 9/2011 |
| WO | WO 2012/017316 A2 | 2/2012 |
| WO | WO 2012/162144 A1 | 11/2012 |
| WO | WO 2013/052029 A1 | 4/2013 |
| WO | WO 2014/018095 A1 | 1/2014 |
| WO | WO 2014/026294 A1 | 2/2014 |
| WO | WO 2014/032540 A1 | 3/2014 |
| WO | WO 2014/070920 A1 | 5/2014 |
| WO | WO 2014/076629 A1 | 5/2014 |
| WO | WO 2014/078564 A1 | 5/2014 |
| WO | WO 2014/123670 A1 | 8/2014 |
| WO | WO 2015/026400 A2 | 2/2015 |

OTHER PUBLICATIONS

Collinsdictionary.com. Definition of lake [retrieved on Jul. 28, 2013]. Retrieved from the Internet: http://www.collinsdictionary.com/dictionary/english/lake.

European Search Report for Application No. 13855790.5, dated Jul. 5, 2016: 8 pages, Oct. 27, 2016.

International Search Report dated Jan. 31, 2017 issued in connection with PCT/US2016/058665; 4 pages.

International Written Opinion dated Jan. 31, 2017 issued in connection with PCT/US2016/058665; 7 pages.

Preliminary Report on Patentability dated May 1, 2018 issued in connection with PCT/US2016/058665; 8 pages.

* cited by examiner

SELF-LIGATING BRACKET

BACKGROUND

Orthodontic brackets are used by orthodontists in preventing and treating facial and dental irregularities, such as malocclusions. Patients seeking treatment from orthodontists are concerned with the presence of crooked teeth, or more particularly dental crowding, flaring, irregularity in tooth alignment, unpleasing tooth appearance, "gummy" smile, and difficulty in chewing, among other issues.

Orthodontic treatment can correct the issues listed above as well as treat other cosmetic and oral irregularities and issues. Issues requiring orthodontic treatment may be the result of discrepancies between the supporting bony structures that house the upper and lower dental arches. Orthodontic treatment can address these discrepancies in order to provide a pleasing smile and a proper chewing function while achieving a long-term stability. Trained and experienced orthodontists seek to reach these goals for the dental patient using various techniques and related equipment and products.

One such product used extensively by orthodontists to correct tooth and jaw irregularities and issues is an orthodontic bracket. Orthodontic brackets are secured to patients' teeth and are used by orthodontists to straighten, move or shift the patient's teeth. Orthodontic brackets are designed to achieve at least two basic objectives: to provide for attachment to a tooth, and to hold an orthodontic archwire. The orthodontic bracket works like an intermediate by connecting an orthodontic archwire to a tooth.

The attachment of the bracket to a tooth transmits a force to a tooth when a resilient orthodontic archwire is bent or twisted, and then brought to engage with the bracket. The archwire coupled to orthodontic brackets mounted on a patient's teeth provides for a mechanical force system that functions to sequentially deliver forces to a patient's teeth, thus directing teeth to the proper positions by the work of the orthodontist.

Conventional orthodontic bracket designs permit the engagement of an archwire into an archwire slot by ligation using elastomeric or wire ligatures wrapped around the tie wings of the bracket. Ligatures or some form of fastening means are essential to secure an archwire in the bracket slot to prevent the archwire from being dislodged.

Several problems exist in the use of wire ligation for both the orthodontist and the patient. The application of the ligating wire requires considerable skill on the part of the orthodontist and long chair time for the patient. Moreover, the archwire must be removed from the orthodontic bracket from time to time for bending or replacement during the course of treatment, calling for repetitive ligating operations and increased patient/orthodontist time.

Traditional wire ligation has other disadvantages as well. Ligation with wire creates undesirable nooks and crevices freely exposed to the harsh oral environment that become traps for food particles, and calculus buildup. Also, because tooth movement occurs along the archwire, binding of the archwire with wire ligatures is undesirable because the binding can introduce unwanted resistant forces during orthodontic treatment. The orthodontist must account for these unwanted resistant forces imparted by the ligating wire. Without careful treatment, the intended corrective tooth movement by the orthodontic mechanical forces may be jeopardized.

Elastomeric ligatures also have disadvantages. Elastomeric ligatures have a tendency to discolor and can rapidly lose their elasticity. Accordingly, the efficiency of elastomeric ligatures in securing the archwire to the orthodontic bracket diminishes over time. Elastomeric ligatures can become ineffective or fail, requiring frequent replacement.

One way to address the disadvantages in traditional ligating methods and products is to incorporate a rapid archwire retention and release mechanism so that the need for ligating wires, elastomeric ligatures, and the like may be reduced, if not completely eliminated. Self-ligating bracket systems attempt to address the disadvantages of traditional ligating methods and products wherein the bracket is capable of retaining the archwire without the need for separate ligating wires or elastomeric ligatures. A self-ligating bracket can be positioned in an open position to allow for insertion or release of the archwire into the archwire slot and a closed position to retain the archwire in the archwire slot.

Problems exist in known self-ligating brackets. Due to complexities of manufacturing and assembly processes associated with orthodontic brackets, a self-ligating bracket with a sliding ligating member is challenging to produce in a cost-effective and efficient manner. Many existing self-ligating designs suffer from high scrap rates.

The difficulties associated with manufacturing and assembling known self-ligating brackets may also result in difficulty in use during orthodontic treatment. In designs in which the self-ligating bracket includes a sliding ligating member, the movable ligating member must be retained in a position such that the ligating member covers the archwire slot. Existing self-ligating designs often fail after only a few cycles of moving the ligating member from an open to a closed position. Further, the force required to open and close known ligating members can vary greatly with different issues. In cases where the force required to move the ligating member is too low, the ligating member may not be sufficiently retained in the closed position and thus cannot reliably retain the archwire. In cases where the force required to move the ligating member to the closed position is too high, an orthodontist may not be able to close the ligating member or the effort to close the ligating member translated into discomfort for the patient during treatment.

Therefore, there exists a need for an improved self-ligating bracket that addresses one or more of the disadvantages and problems discussed above. In one embodiment, the present disclosure describes a self-ligating bracket that includes a reliable way of retaining an archwire without the need for separate wire or elastomeric ligatures. The present disclosure also describes a self-ligating bracket that is more easily manufactured and reduces the scrap rate from that of existing designs. Still further, the present disclosure includes a repeatable, durable design for retaining or biasing the ligating member in the open or closed position.

Still another advantage is the ease of use in the clinical environment. This is especially evident in the case of lingual orthodontic brackets. Although the majority of orthodontic brackets are placed on the outer surface of teeth (labial surface), that is the area facing the labial tissue of the patient or the area generally visible to others, some patients opt for a cosmetic approach towards treatment. Lingual brackets allow for orthodontic treatment, not visibly apparent to others, where the bracket is bonded on a lingual surface of the tooth. Lingual brackets are particularly difficult to manipulate by an orthodontist due to limited access within the patient's mouth. The present disclosure describes an easy to use self-ligating bracket that permits easy manipulation of the ligating member by an orthodontist.

SUMMARY

In one embodiment, an orthodontic bracket includes a bracket body with a recess on its top surface and an archwire slot adapted to receive an orthodontic wire. The orthodontic bracket also includes a ligating member with a projection extending from the bottom surface into the recess on the bracket body. The ligating member is movably connected to the bracket body for retaining the orthodontic wire in the archwire slot when the ligating member is moved from an open position to a closed position. The orthodontic bracket also includes a discrete spring positioned in the recess on the bracket body such that a force is required to move the ligating member from the open position to the closed position.

In another embodiment, the projection of the orthodontic bracket extends into the recess and contacts the discrete spring when the ligating member is moved from the open to the closed position.

In another embodiment, the discrete spring is either annular, discoidal, oval, helical, round or curved in shape.

In another embodiment, the recess limits the movement of the discrete spring when the ligating member is moved from the open position to the closed position.

In another embodiment, the recess on the top surface of the bracket body of orthodontic bracket includes a spring portion with an arcuate edge and a guide portion with a linear edge.

In another embodiment, the recess of the orthodontic bracket includes a spring portion with an arcuate edge concentric with a portion of the discrete spring. The recess also contains a guide portion with a linear edge parallel with the path of travel of the projection from the open position to the closed position.

In another embodiment, the recess of the orthodontic bracket also includes a relief portion with a second arcuate edge such that the discrete spring extends into the relief portion when compressed by the projection.

In another embodiment, the depth of the recess of the orthodontic bracket is greater than the thickness of the discrete spring.

In another embodiment, the relief portion of the recess is elliptically shaped and overlaps the spring portion of the recess where the major axis is parallel to the path of travel of the projection from the open position to the closed position.

In another embodiment, the orthodontic bracket includes a surface with a recess, where the recess includes a spring portion with a first edge which may be arcuate and a guide portion with a second edge which may be linear. The recess further includes a discrete spring in the spring portion of the recess. A projection extends from a second surface into the recess adjacent to the second edge where the bracket is configured such that the discrete spring is compressed by the projection when the first surface and second surface move relative to each other.

In another embodiment, the orthodontic bracket includes a bracket body with a projection extending from a top surface and an archwire slot adapted to receive an archwire, and a ligating member including a recess on a bottom surface. The ligating member is movably connected to the bracket body for retaining an orthodontic wire in the archwire slot when the ligating member is moved from an open position to a closed position. The orthodontic bracket also includes a discrete spring positioned in the recess on the ligating member such that a force is required to move the ligating member from the open position to the closed position.

BRIEF DESCRIPTION OF THE DRAWINGS

Certain embodiments are shown in the drawings. However, it is understood that the present disclosure is not limited to the arrangements and instrumentality shown in the attached drawings, wherein.

DETAILED DESCRIPTION

Figure 1:
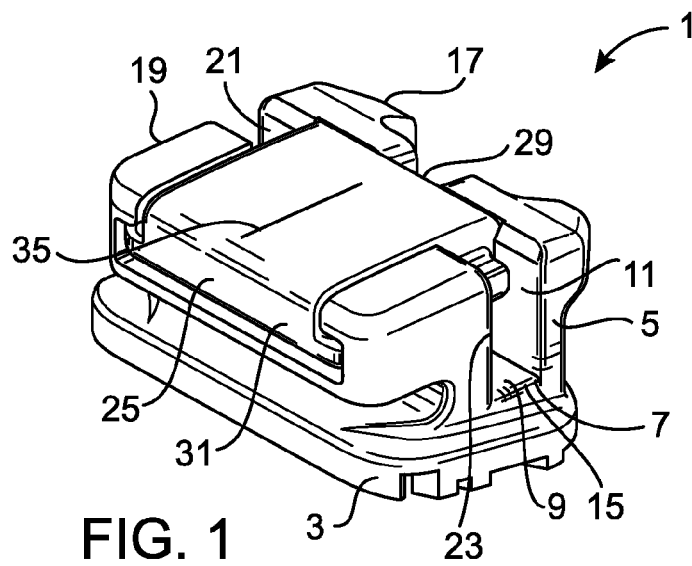
FIG. 1 is an illustration of one embodiment of a self-ligating bracket.

For the purposes of promoting and understanding the principles disclosed herein, references are now made to the preferred embodiments illustrated in the drawings and specific language is used to describe the same. It is nevertheless understood that no limitation of the scope is thereby intended. Such alterations and further modifications in the illustrated device and such further applications of the principles disclosed as illustrated herein are contemplated as would normally occur to one skilled in the art to which this disclosure relates.

As shown in FIG. 1, one embodiment of self-ligating bracket 1 may include a bracket base 3 for attachment to a tooth surface and a bracket body 5 with various structures for the engagement and retention of an archwire. Bracket base 3 may have a concavely contoured surface and may include an indented bottom to enhance its attachment to a tooth. Bracket base 3 and bracket body 5 are connected to one another and may be integrally formed, molded together, or welded.

Self-ligating bracket 1 may also include bracket body 5. Bracket body 5 may include gingival extension 17, occlusal extension 19 and support surface 7 that define archwire slot 11. Archwire slot 11 is sized to receive an orthodontic archwire, and includes beveled edges 15 at the edge of the archwire slot base 9 and sides on the mesial and distal edges. Beveled edges 15 serves to reduce the likelihood that an orthodontic wire becomes damaged when it is received in archwire slot 11. Gingival extension 17, occlusal extension 19 and support surface 7 are configured such that archwire slot 11 runs generally parallel to the occlusal plane (an imaginary plane constructed by connecting the edges of the front teeth and the cuspids of the posterior teeth). Archwire slot 11 may be angularly oriented across the bracket when desired per the prescriptive torque, tip and angulation.

Figure 3:
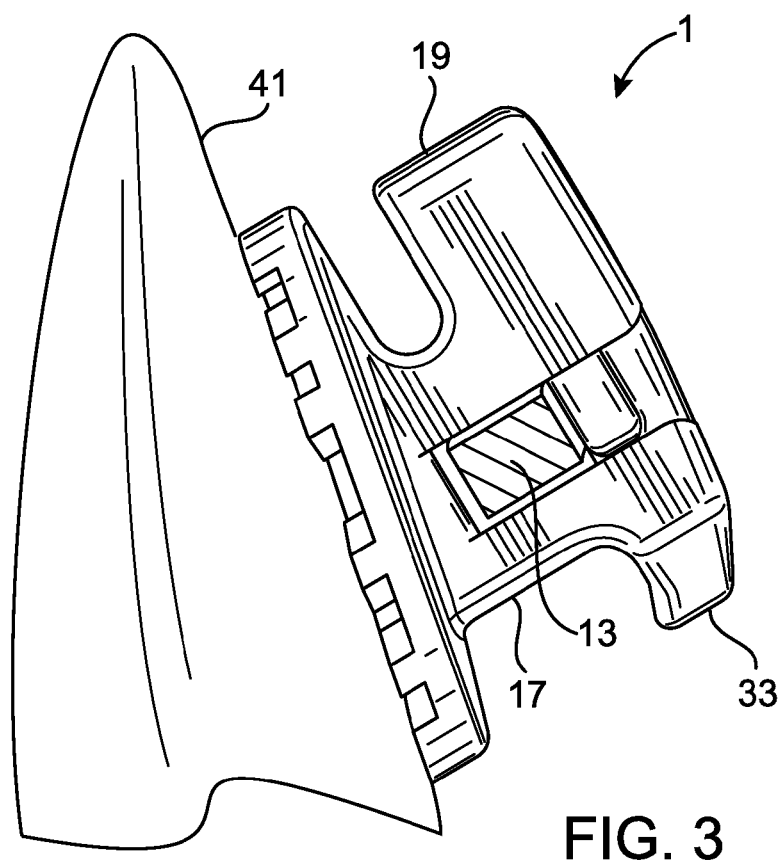
FIG. 3 is a side view of one embodiment of a self-ligating bracket of the present disclosure as mounted on the lingual surface of a tooth with an archwire.

Gingival extension 17 and occlusal extension 19 of bracket body 5 extend upward from bracket base 3. Gingival extension 17 or occlusal extension 19 may include at least one tie wing. A tie wing can be positioned on one or both the gingival and occlusal sides of the bracket body 5. In one embodiment, bracket body 5 may include gingival tie wing 33 at the gingival extension 17. Gingival tie wing 33 can be angled towards the surface of the tooth, such as is depicted in FIG. 3.

As previously described, bracket body 5 may include gingival extension 17, occlusal extension 19 and support surface 7 that define archwire slot 11. More specifically, gingival extension 17 includes transversely oriented gingival wall 21 and occlusal extension 19 includes occlusal wall 23 that together with support surface 7 define archwire slot 11. An orthodontic wire that is received into archwire slot 11 is surrounded by these three surfaces. Archwire slot 11 is open for receiving or removing an orthodontic archwire when ligating member 25 is in the open position. As will be further described, ligating member 25 covers archwire slot 11 and retains a received orthodontic wire when ligating member 25 is moved to the closed position. Archwire slot 11 is constructed so as to accommodate a rounded, rectangular or square orthodontic archwire.

Referring back to gingival tie wing 33 on gingival extension 17, gingival tie wing 33 may include gingival indentation 29 (as shown in FIG. 1) sufficiently large for insertion of a tool such as an opening tool or scaler. Gingival indentation 29 is a gap along a top surface of gingival extension 17 that extends downwardly toward bracket base 3 and permits access to one end of ligating member 25 when ligating member 25 is in the closed position. Gingival indention 29 permits an orthodontist or other clinician to apply force and move the ligating member 25 in the occlusal direction when opening the archwire slot 11. Closure of the archwire slot 11 can be achieved by pressing the ligating member 25 on the occlusal edge 31 in a direction toward gingival extension 17. Closure of ligating member 25 can be accomplished with either a dental tool or a clinician's fingertips.

Figure 6:
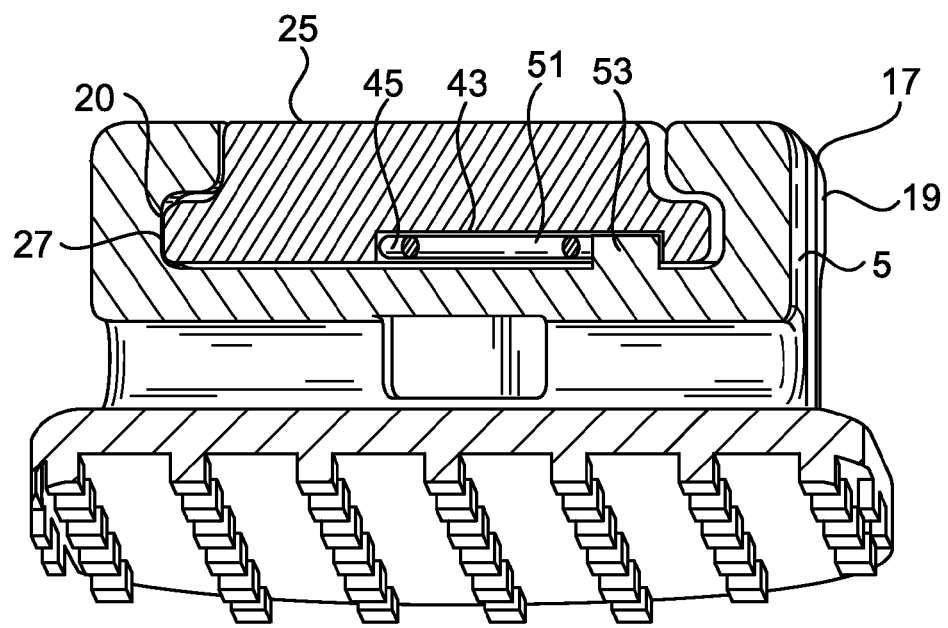
FIG. 6 is a sectional front view of one embodiment of the self-ligating bracket.

Self-ligating bracket 1 also includes ligating member 25. Ligating member 25 is movably connected to bracket body 5 at occlusal extension 19. As shown in FIG. 1, ligating member 25 may be a generally rectangular member. Ligating member 25 may also include one or more rails that are received into a complimentary portion of ligating member channel 27 (as shown in FIG. 6). As can be seen in the embodiment shown in FIG. 1, the rails on ligating member 25 are configured such that a top surface of ligating member 25 is substantially coplanar or at least flush with top surfaces of two stanchions 20 on occlusal extension 19. The two stanchions 20 on occlusal extension 19 cover a portion of the rails on ligating member 25 when ligating member 25 is received into ligating member channel 27 such that ligating member is permitted to move in an occlusal-gingival direction only.

In one embodiment, ligating member 25 may have a smooth convex outer surface coplanar with the outer surface of the bracket body 5. The smooth, polished surface of ligating member 25 is designed for ease in maintaining good oral hygiene while deterring bacterial adherence and plaque accumulation. Ligating member 25 may also include mark 35 along the centerline of ligating member 25 to assist a clinician in aligning the bracket with the axial inclination of a clinical crown tooth, during the bracket bonding procedure. Mark 35 can be either a permanent or temporary indicator that is molded, machined or painted onto ligating member 25.

Figure 2:
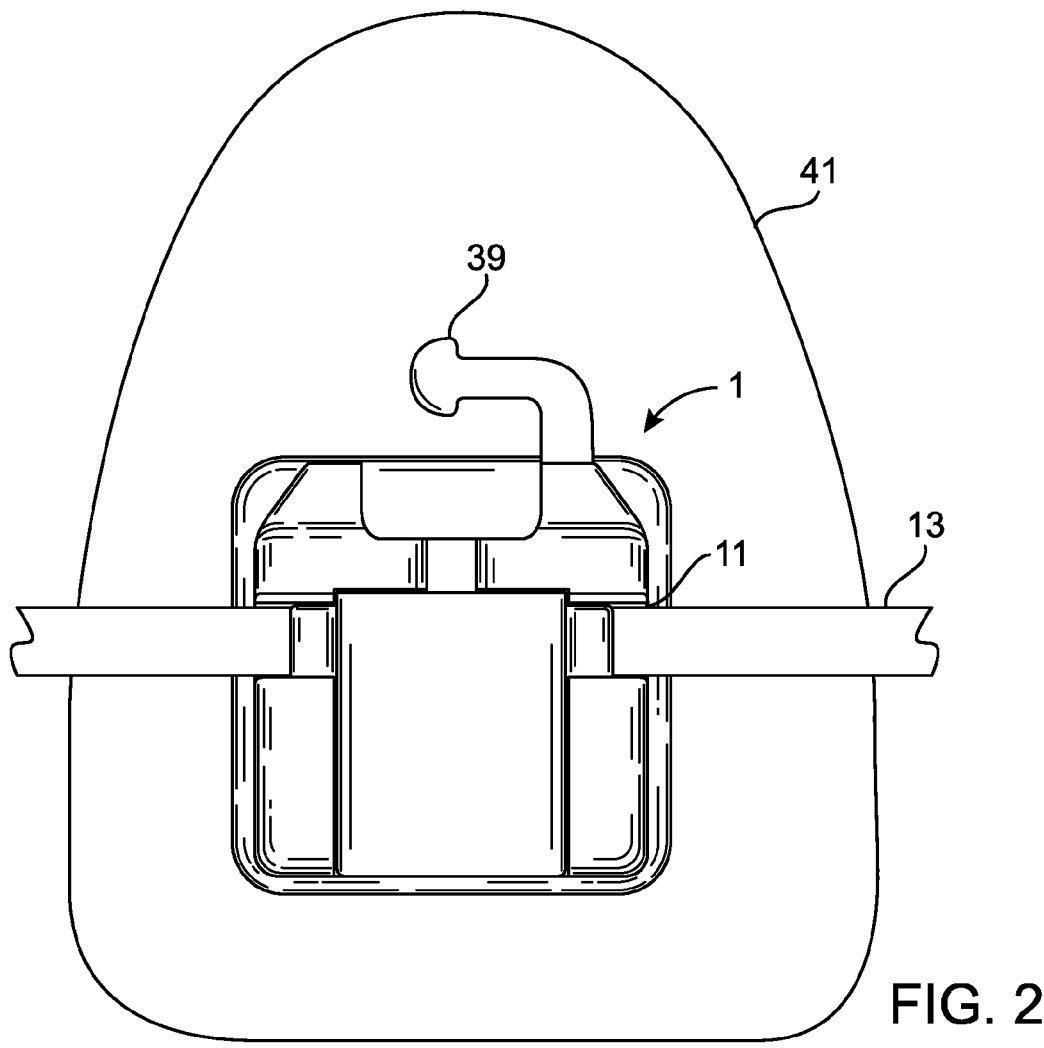
FIG. 2 is a top view of one embodiment of a self-ligating bracket of the present disclosure as mounted on the labial surface of a tooth with an archwire.

FIG. 2 shows an embodiment of self-ligating bracket 1 as positioned on a labial surface 37 of a patient's upper tooth. As shown, self-ligating bracket 1 can retain archwire 13 in archwire slot 11 when ligating member 25 is closed. Self-ligating bracket 1 may also include hook 39. Other auxiliary devices may also be included on self-ligating bracket 1.

Figure 4:
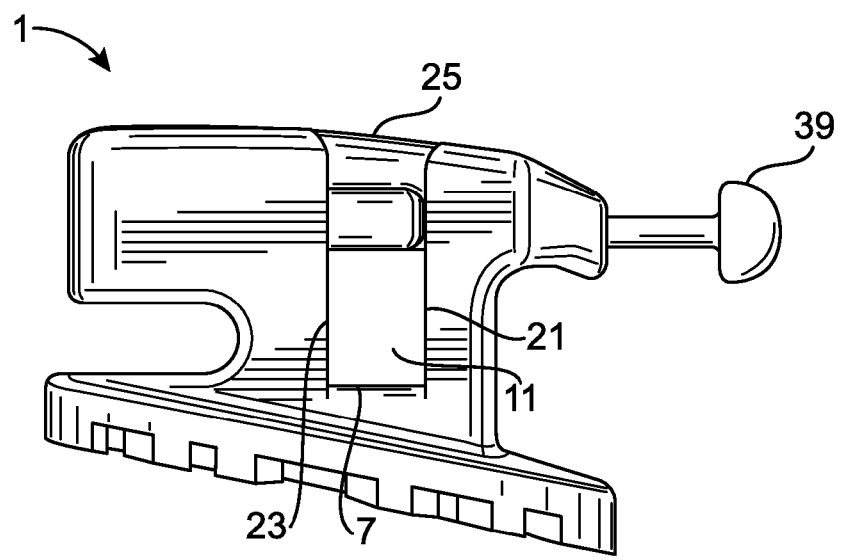
FIG. 4. is a side view of one embodiment of the self-ligating bracket in the closed position.
Figure 5:
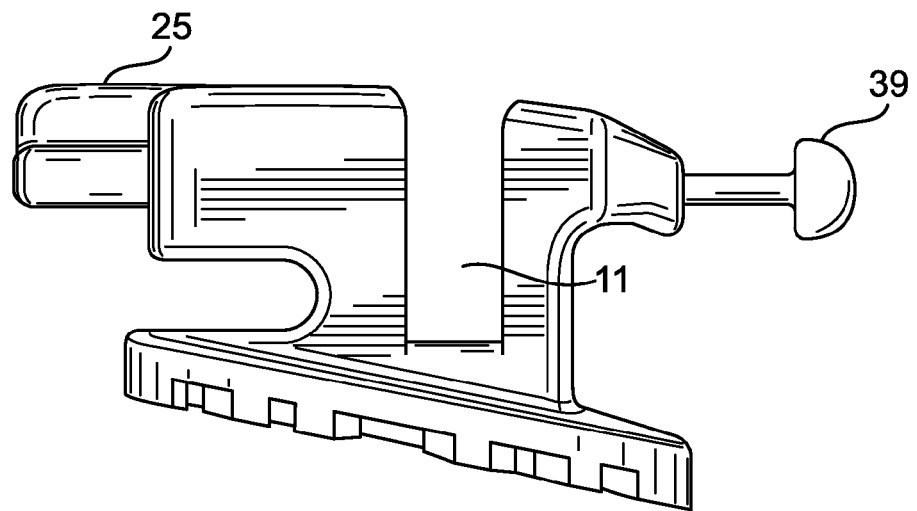
FIG. 5 is a side view of one embodiment of the self-ligating bracket in the open position.

FIG. 3 shows an embodiment of self-ligating bracket 1 as positioned on a lingual surface 41 of a patient's lower tooth. In this figure, self-ligating bracket 1 is shown mounted to a tooth surface in the closed position with an archwire 13. As can be appreciated, ligating slide 25 prevents archwire 13 from being removed from archwire slot 11. In FIG. 4, ligating slide 25 is in a closed position and archwire 13 has been removed from archwire slot 11. In FIG. 5, ligating slide 25 is in an open position and archwire 13 has been removed from archwire slot 11.

Figure 7:
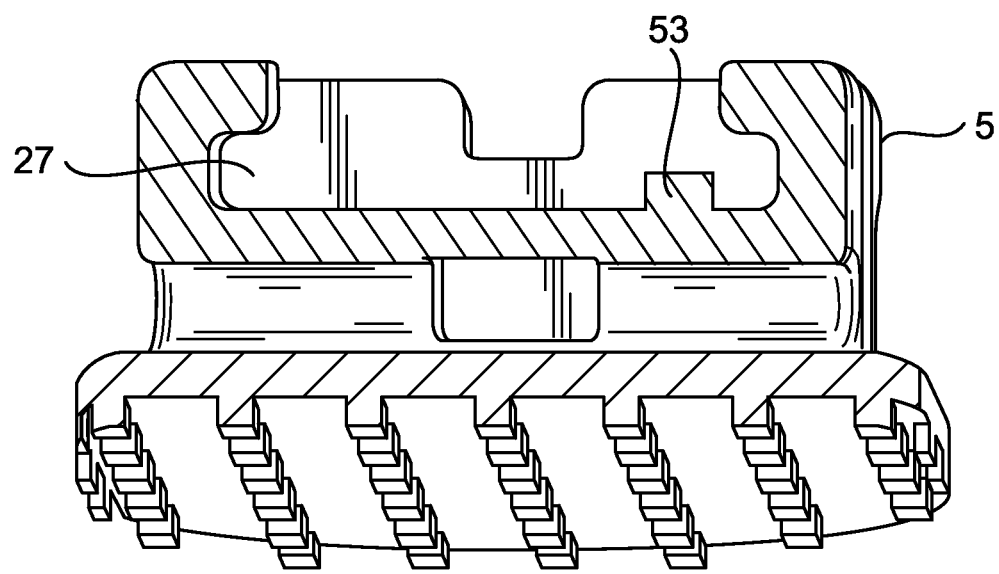
FIG. 7 is a sectional front view of one embodiment of the self-ligating bracket without the ligating member.
Figure 8:
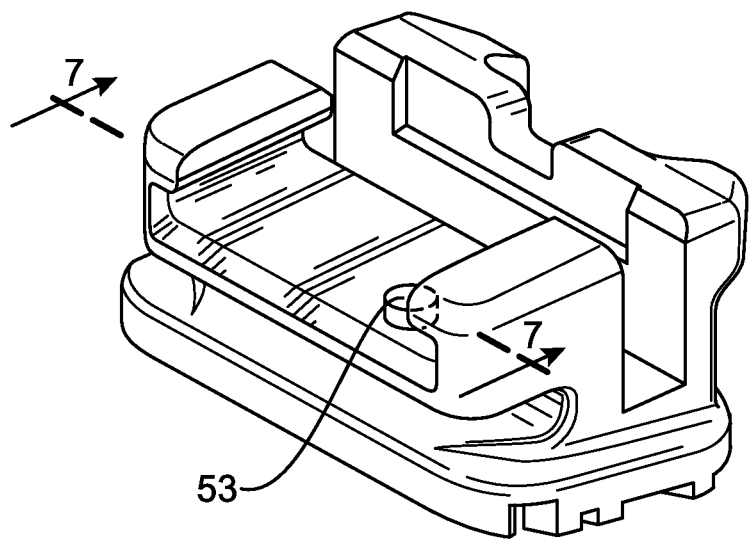
FIG. 8 is an isometric view of one embodiment of the self-ligating bracket without the ligating member.
Figure 9:
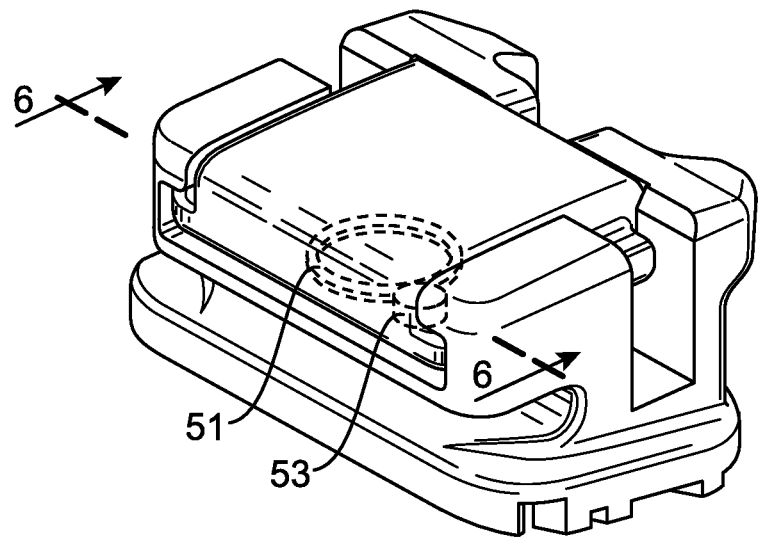
FIG. 9 is an isometric view of one embodiment of the self-ligating bracket with the spring and projection shown in hidden lines.

As shown in FIGS. 6-7, self-ligating bracket 1, in one embodiment, is configured to receive ligating member 25 in ligating member channel 27. Ligating member channel 27 can be positioned in the central front part of occlusal extension 19. Ligating member channel 27 may be defined by two opposed inwardly projecting side walls located on occlusal extension 19 located below two stanchions. Ligating member 25 received in ligating member channel 27 is permitted to move in a generally linear motion along ligating member channel 27 toward gingival extension 17 until ligating member 25 encounters an occlusal facing surface of gingival extension 17. Ligating member channel 27 may exhibit a wide front open end with two inwardly facing slots retaining and enabling the ligating member 25 and the rails contained thereon to travel from an open position to a closed position. Ligating member channel 27 may have other suitable shapes and profiles with a suitable complimentary shape or profile on ligating member 25.

As can be appreciated, ligating member 25 can move in ligating member channel 27 from an open to a closed position. Depending on the needs of the clinician, it is desirable that the slide be retained in the open position, such as during treatment, or in the closed position, such as after an archwire has been inserted between treatment visits. In order to maintain the ligating member in either the open or closed position, self-ligating bracket 1 includes a retention mechanism that may include spring 51 and projection 53. Spring 51 and projection 53 interact to prevent undesired movement of ligating member 25 relative to bracket body 5.

In one embodiment, spring 51 is a discrete annular resilient member. In this embodiment, spring 51 is a separate member that is not integrally formed or machined as part of ligating member 25 or any other element of self-ligating bracket 1. In a preferred embodiment, spring 51 is 0.5-1.5 mm in outside diameter, has a height of 0.15-2 mm and is made of a nickel-titanium alloy. This size of spring 51 may vary depending of the size of the self-ligating bracket and the size of the tooth on which the bracket is intended to be used. Spring 51 may be formed from a piece of wire, cut from a sheet of material or be a slice of tubing. Still other methods of manufacture of spring 51 are also contemplated. Further, in other embodiments, spring 51 can have other shapes such as discoidal, oval, helical, semi-circular, round or curved, or other suitable configurations. Spring 51 can also be made of other suitable metals, alloys, plastics, rubbers, composites or other resilient natural or synthetic materials.

As stated earlier and as shown in FIG. 7, bracket body 5 may include projection 53 extending from a top surface of the bracket body 5. Projection 53 is adapted to interface with recess 43 and spring 51 in ligating member 25. In one embodiment, projection 53 is a cylindrical pin integrally formed with or molded in bracket body 5. Projection 53, however, may be made of any suitable shape or profile and may be separately attached to bracket body 5. Since projection 53 will be moving inside of recess 43 and contacting spring 51 as will be further explained, a smooth surface of projection 53 is desirable.

Figure 10:
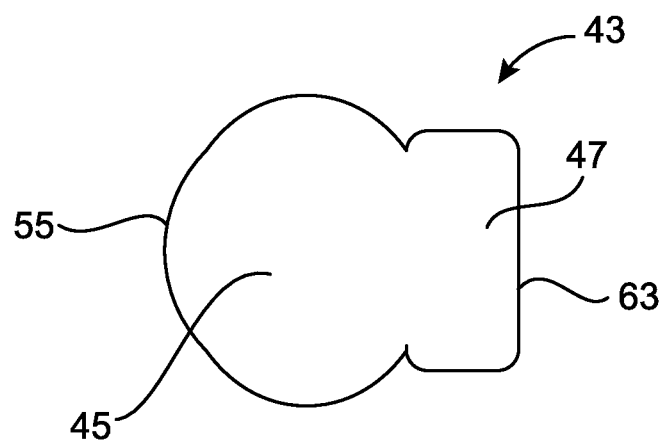
FIG. 10 is a view of the recess without the spring.
Figure 11:
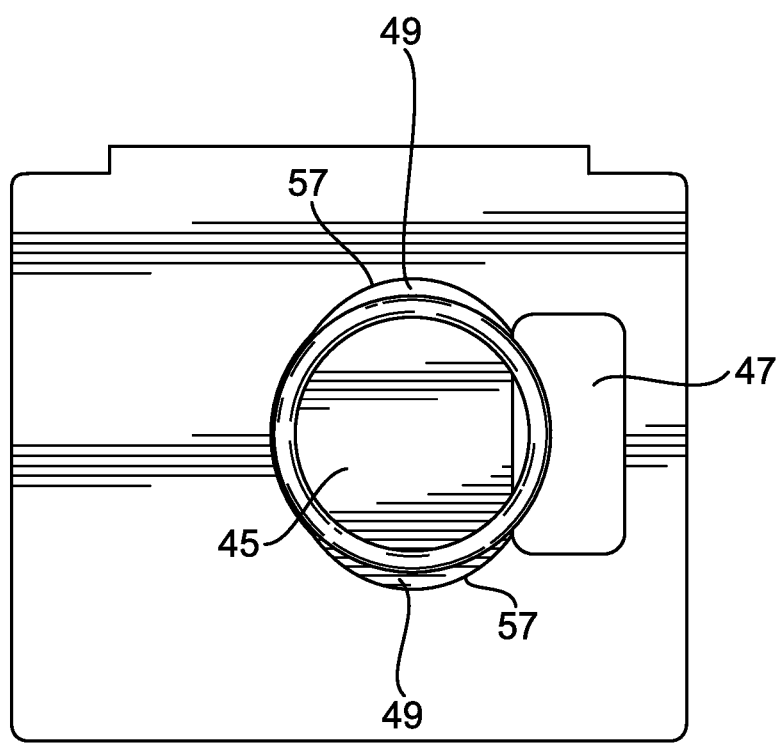
FIG. 11 is a bottom view of one embodiment of the ligating member with the spring.

As shown in FIGS. 10-14, projection 53 interfaces with recess 43 and interacts with spring 51. In one embodiment, recess 43 is positioned on a bottom surface of ligating member 25 that is located contiguous to the top surface of bracket body 5 on which projection 53 resides. Recess 43 may include spring portion 45 defined, in part, by a first edge 55 and a guide portion 47 defined, in part, by a second edge 63. In one embodiment, first edge 55 may be arcuate and second edge 63 may be linear. As shown in FIG. 10, spring portion 45 provides an area for positioning of the spring 51. First edge 55 of the recess 43 may be concentric with a portion of the spring 51, thereby providing a surface for proper positioning and alignment of the spring 51 in recess 43. In one embodiment, the height of the spring 51 is less than the depth of recess 43 at the spring portion 45 such that spring 51 is free to "float" in recess 43 unless otherwise held in position. This configuration minimizes resistance when the ligating member is moved from open to the closed position, and vice versa. As shown in the embodiment shown in FIG. 6, spring 51 with a height less than the depth of the recess 43 essentially allows for the spring to "free-float" above the labial facing surface of bracket body 5. As used herein, the term "free-float" means that the spring is not fixed to any portion of the self-ligating bracket 1. Rather, the spring is permitted to move within recess 43.

One advantage of having a free-floating spring is that this configuration reduces instances of spring breakage by reducing or minimizing stress points along the entirety of the spring. In the embodiment shown in FIG. 11, spring 51 is free to move or rotate within the spring portion 45 or recess 43.

In other embodiments, the guide portion 47 of recess 43 can be a through-hole in the ligating member instead of a mere recess in the ligating member.

In other embodiments, spring 51 and recess 43 can have other relative configurations. In one embodiment, spring 51 is press fit within spring portion 45. In another embodiment, spring 51 is initially compressed when positioned and essentially decompresses or decoils until it abuts against first edge 55 of the recess. The approach is especially useful where the spring has the opportunity to expand into spring portion 45 once assembled into bracket 1. In another embodiment, spring 51 may be held in position with a staking or similar process in which an edge of spring portion 45 is deformed and one or more projections extend from the first edge 55 or from an inner surface of the recess 43 into the spring portion 45 to hold spring 51 in position.

Figure 18:
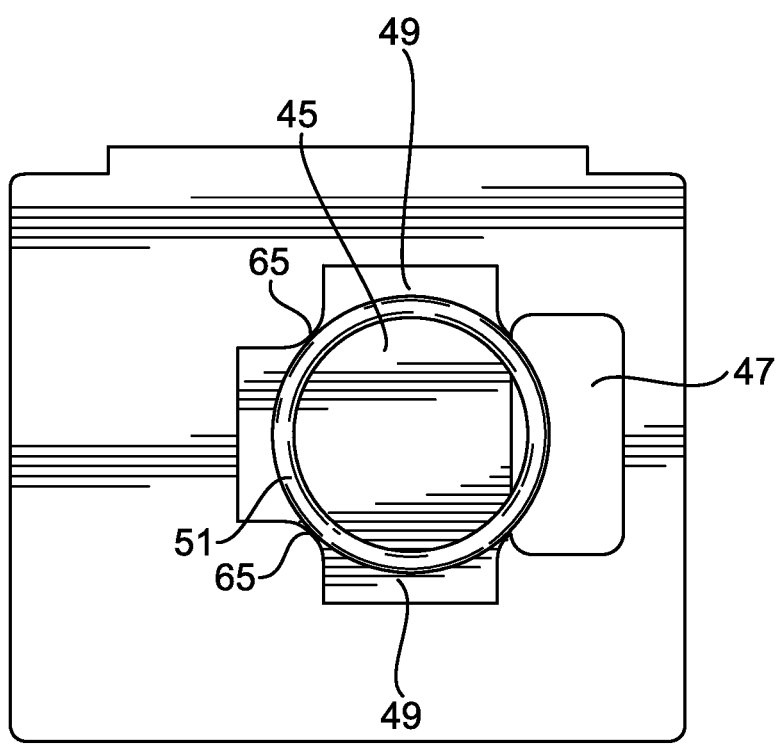
FIG. 18 is another embodiment of the ligating member with recess and spring.

As shown in FIGS. 11-14, recess 43 further includes relief portion 49 defined by at least a third edge 57, which may be arcuate. As can be appreciated, spring 51 extends into the relief portion 49 when spring 51 is compressed by projection 53. As further shown in FIGS. 11-14, relief portion 49 can be shaped as a portion of an ellipse with a long axis parallel to the direction of travel of the projection 53 from the open to the closed position. Other suitable configurations of relief portion 49 can also be used (e.g. as depicted in FIG. 18). Relief portion 49 allows the spring 51 to extend into the relief portion 49 when compressed without creating large stress concentrations. In addition, the relief portion 49 limits how far the spring 51 can distend along the long axis of the expansion area by providing a hard stop defined by the third edge 57.

Figure 12:
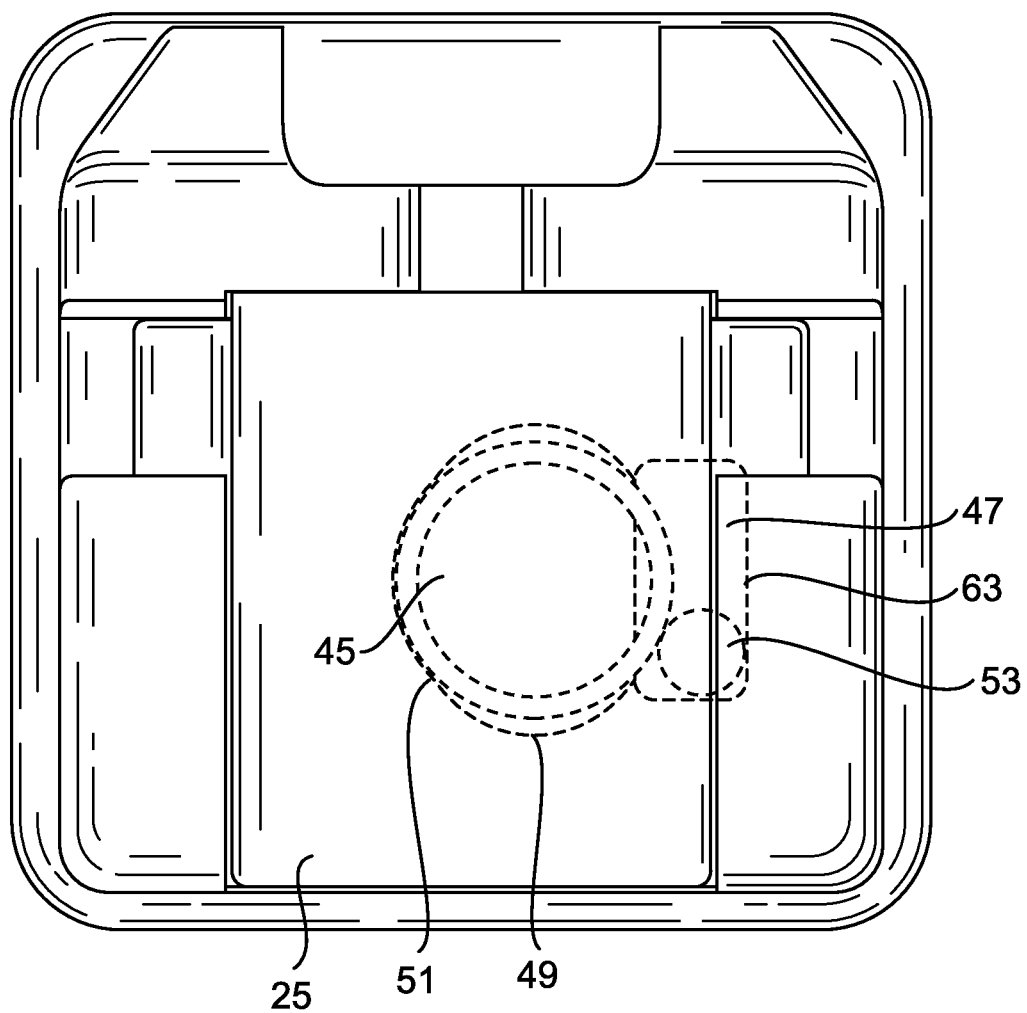
FIG. 12 is a top view of one embodiment of the self-ligating bracket with the ligating member in the closed position.
Figure 13:
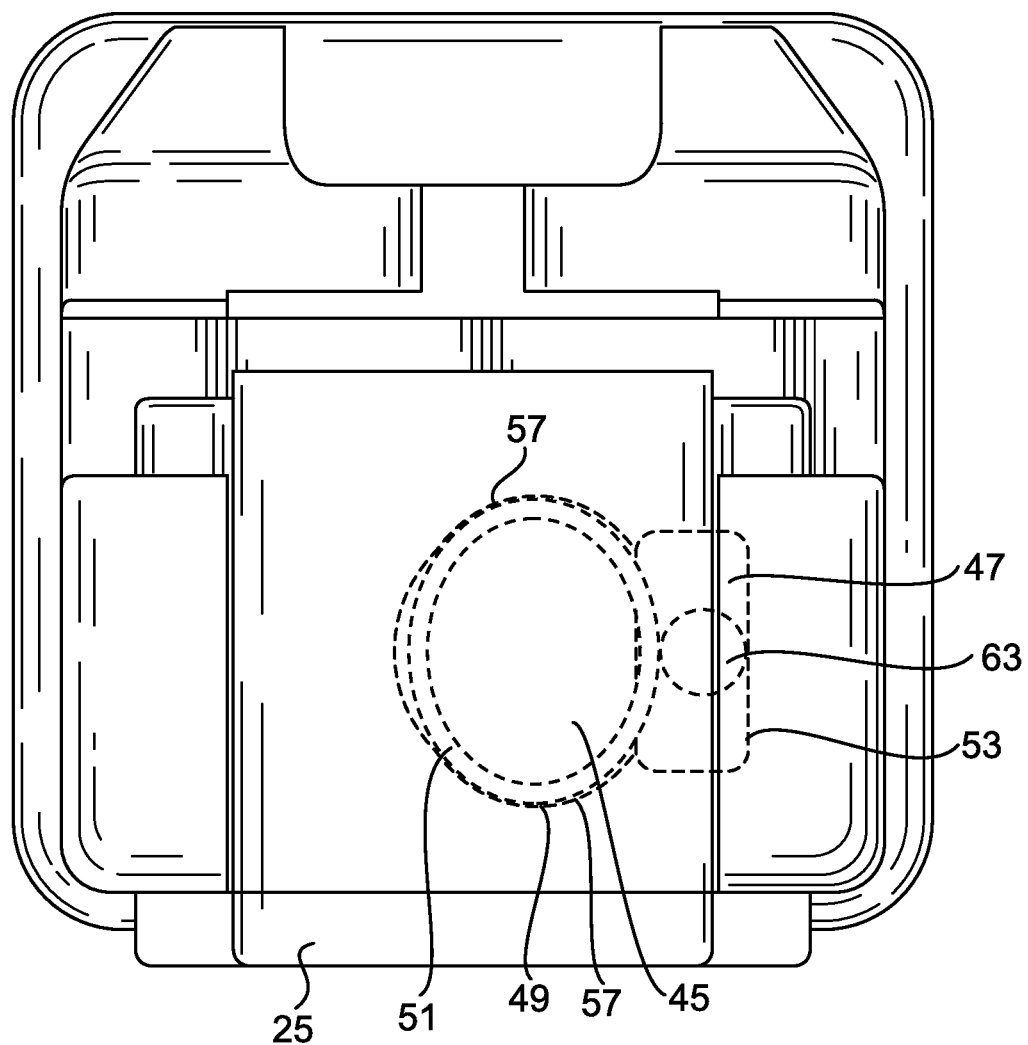
FIG. 13 is a top view of one embodiment of the self-ligating bracket with the ligating member halfway between the open and the closed position.
Figure 14:
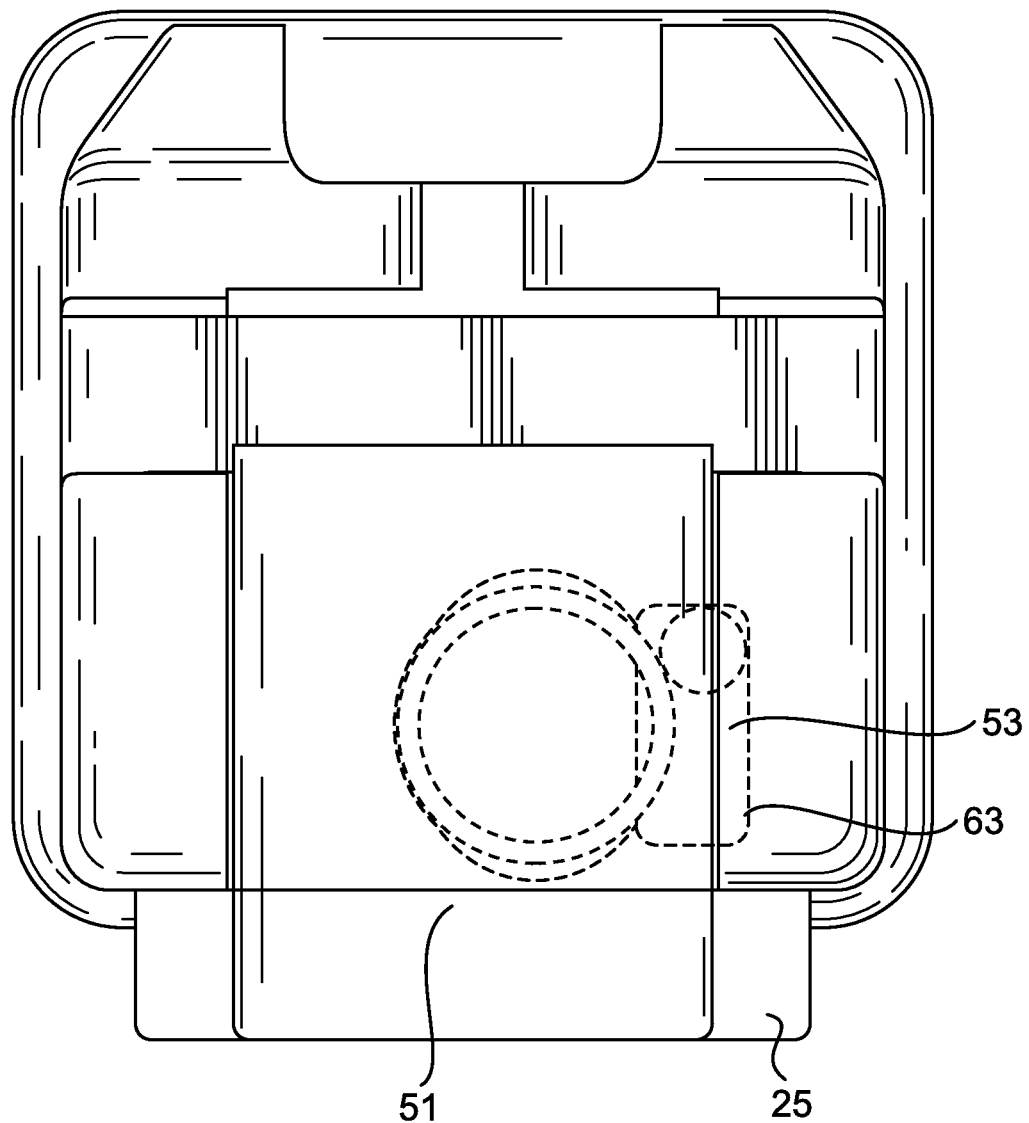
FIG. 14 is a top view of one embodiment of the self-ligating bracket with the ligating member in the open position.

Recess 43 also includes guide portion 47. Projection 53 interfaces with guide portion 47. As shown in FIGS. 12-14, as ligating member 25 moves from an open position to a closed position, projection 53 travels along guide portion 47 substantially parallel to second edge 63. In another embodiment, second edge 63 is substantially parallel to the center axis of ligating member channel 27. Projection 53 extends into the guide portion 47 of the recess 43. In another embodiment, the guide portion 47 serves as a hard stop to limit the travel of the ligating member when moving from the closed position to the open position, wherein the projection 53 abuts inner surface of guide portion to retain the ligating member 25 within bracket body 5 (shown in FIG. 14). Furthermore, the guide portion 47 sufficiently overlaps the spring portion 45 such that the projection 53 interferes with the spring 51 along the path of travel. As can be appreciated, as projection 53 moves from a first position corresponding to the open position of ligating member 25 to a second position corresponding to the closed position of ligating member 25, spring 51 compresses and extends into relief portion 49, permitting projection 53 to travel from the first position to the second position. Force is required to compress the spring with sufficient force so as to allow projection 53 to move from the open position to the closed position, or vice versa. In this manner, recess 43, spring 51 and projection 53 interact as a retention mechanism to hold ligating member in either the open position or the closed position.

The interaction of the elements of the retention mechanism of self-ligating bracket 1 is illustrated in FIGS. 12-14. FIG. 12 depicts ligating member in a closed position. The spring 51 is in a semi-compressed or uncompressed state with projection 53 in a first position. The recess and spring of the retention mechanism may overlie the archwire slot in the closed position. FIG. 13 depicts ligating member halfway between the open position and the closed position. The spring 51 is in a compressed state with projection 53 halfway through the path of travel from a first position to a second position. As shown, spring 51 has extended into the relief portion 49 in this state. The recess 43 limits the movement of the discrete spring when the ligating member is moved from the open position to the closed position. In one embodiment, this limitation is in a direction perpendicular to the path of travel of the ligating member 25. FIG. 14 depicts the ligating member in an open position. The spring is in a semi-compressed or uncompressed state with projection 53 in a second position.

Figure 15:
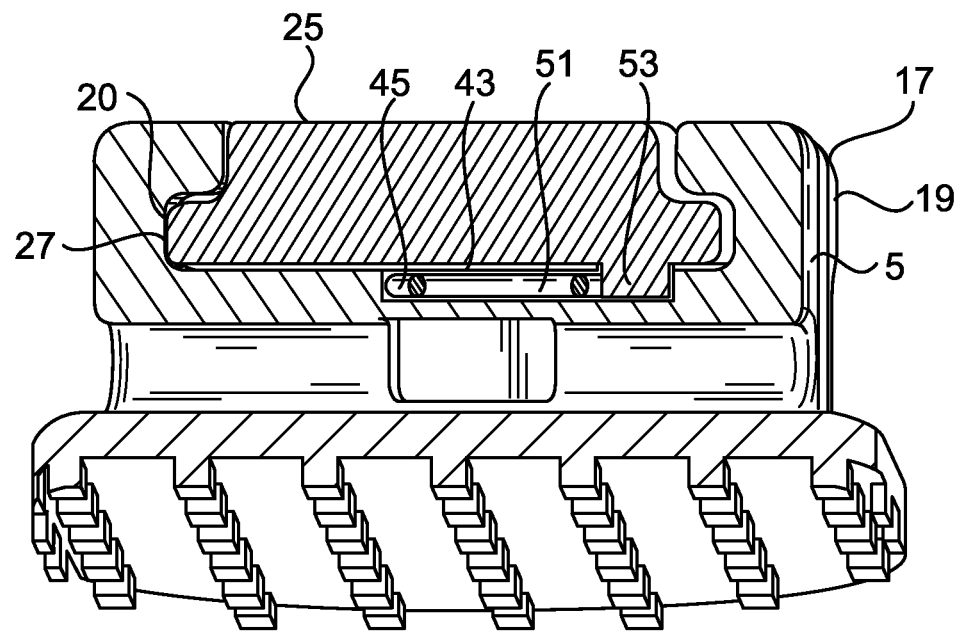
FIG. 15 is a sectional front view of another embodiment of the self-ligating bracket.
Figure 16:
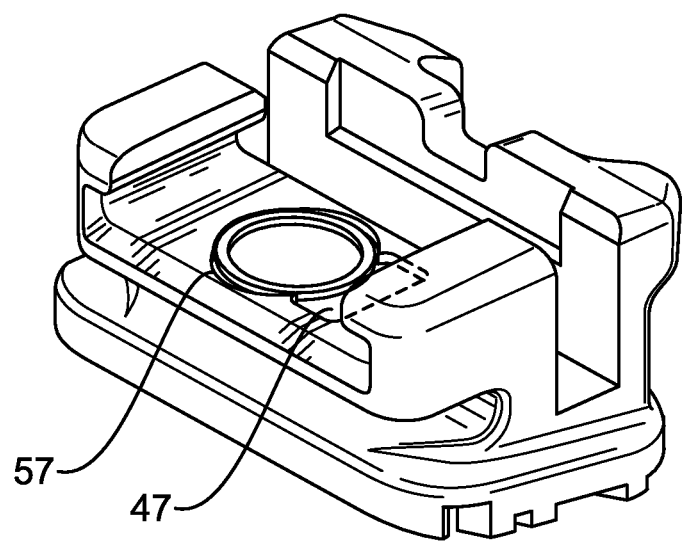
FIG. 16 is an isometric view of another embodiment of the self-ligating bracket without the ligating member.
Figure 17:
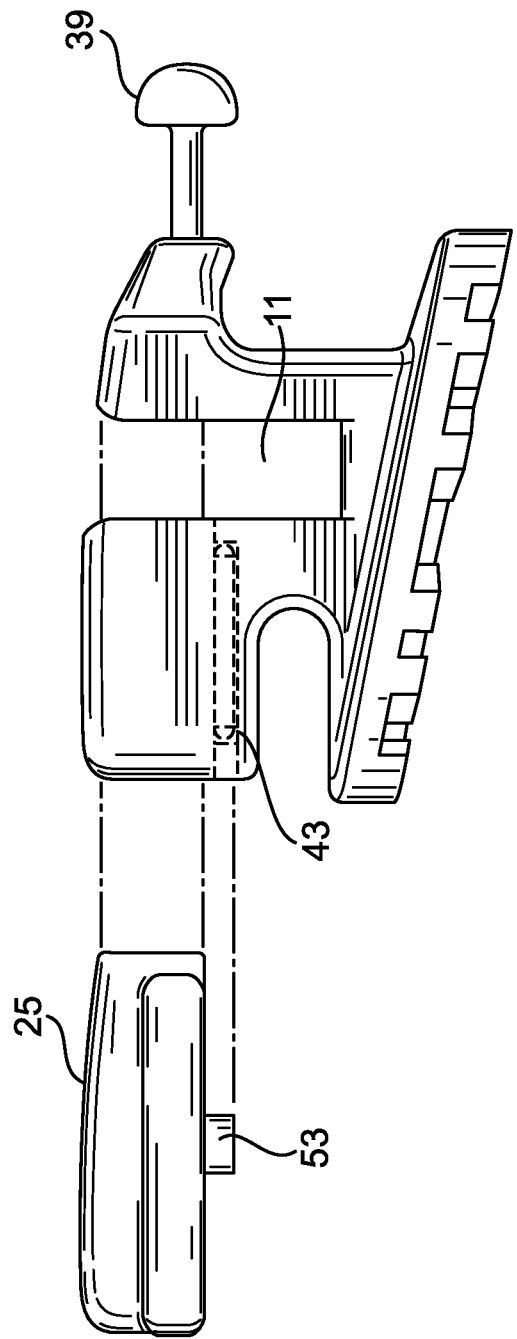
FIG. 17 is a side view of the self-ligating bracket of another embodiment with the ligating member disassembled from the bracket body.

As previously described, projection 53 is located on bracket body 5 and recess 43 and spring 51 are positioned on ligating member 25. This configuration can also be reversed in other embodiments. Specifically, projection 53 can be integrally formed or connected to ligating member 25, and recess 43 with spring 51 can be positioned on bracket body 5. In this reversed configuration, as shown in FIGS. 15-17, the retention mechanism interacts to perform the same function. The projection 53 may be molded as part of the ligating member 25, or attached thereafter by welding, adhesive, mechanical attachment, or by any other means. FIGS. 15 and 16 further depict the spring portion 45, relief portion 57 and guide portion 47 of the recess 43. Irrespective of the configuration, the invention is an archwire retention mechanism for bracket assembly with ligating member 25 wherein a first surface with recess 43 includes a spring 51 located within the recess, and a projection extending from a second surface into the recess such that the spring is compressed by the projection when the first surface and second surface move relative to each other. FIG. 17 depicts the bracket assembly in a partially exploded view where the ligating member 25 is disassembled from the bracket body 5 to further demonstrate respective components of the retention mechanism.

FIG. 18 is yet another embodiment of the retention mechanism showing the recess comprising of a spring portion 45, relief portion 49 and guide portion 47. Here the recess 43, although a different configuration, limits the movement of the spring 51 in the spring portion 45 when the ligating member is moved from the open position to the closed position. In FIG. 18, the spring 51 would extend into relief portions 49 when compressed by the projection 53 (not shown). This occurs as edges 65 of recess 43 in spring portion 45 provide a hard stop limiting movement of the spring 51 when compressed (similar to FIG. 13). Although the configuration of this embodiment has been shown where the recess 43 resides in ligating member 25, the configuration may be reversed where the recess resides in bracket body 5 and the projection resides in ligating member. It is understood that the present disclosure is not limited to the arrangements and instrumentality shown in the attached drawings.

Self-ligating bracket 1 can be manufactured using any suitable manufacturing method including machining, casting, metal injection molding (MIM), plastic injection molding (PIM) or ceramic injection molding (CIM). Self-ligating bracket 1 can be made of any suitable material such as stainless steel, gold, nickel titanium, nickel-free titanic alloy, ceramic, cobalt chromium, plastic or combinations thereof. In one preferred embodiment, self-ligating bracket 1 is made of stainless steel.

The orthodontic bracket 1, unless otherwise indicated, is described herein using a reference frame attached to a labial surface of an anterior tooth. Consequently, as used herein, terms such as labial, lingual, mesial, distal, occlusal and gingival used to describe the bracket are relative to the chosen reference frame. The embodiments of the invention, however, are not limited to the chosen reference frame and descriptive terms, as the orthodontic bracket may be used on other teeth and in other orientations within the oral cavity. For example, the bracket may also be coupled to the lingual surface of the tooth and be within the scope of the invention. Those of ordinary skill in the art will recognize that the descriptive terms used herein may not directly apply where there is a change in reference frame. Nevertheless, embodiments of the invention are intended to be independent of location and orientation within the oral cavity and the relative terms used to describe embodiments of the orthodontic bracket are merely to provide a clear description of the embodiments in the drawings. As such, the relative terms, labial, lingual, mesial, distal, occlusal and gingival are in no way limiting the invention to a particular location or orientation.

The terms and expressions which have been employed in the foregoing specifications are used therein as terms of description and not of limitation, and there is no intention in the use of such terms and expression of excluding equivalence of the features shown and described portions thereof, it being recognized that the scope of the invention is defined and limited only by the claims which follow.

The invention claimed is:

1. An orthodontic bracket comprising:
a bracket body with a lingual surface opposite a top surface, the bracket body including a recess on the top surface and an archwire slot;
a ligating member with a bottom surface proximate the top surface, the bottom surface including a projection extending substantially perpendicularly from the bottom surface into the recess, the ligating member movably connected to the bracket body for retaining an orthodontic wire in the archwire slot when the ligating member is moved in a direction of travel from an open position to a closed position; and
a discrete free-floating spring positioned in the recess such that a force is required to move the ligating member from the open position to the closed position, wherein the recess further comprises a relief portion between the discrete free-floating spring and the bracket body in the direction of travel and the discrete free-floating spring is compressed into the relief portion by the projection when the ligating member is moved from the open position to the closed position;
wherein the recess includes a spring portion defined by a first edge and a guide portion defined by a second edge and the relief portion is defined by at least a third edge that is elliptically shaped and overlaps the spring portion with a major axis parallel to the direction of travel of the projection from the open position to the closed position.

2. The orthodontic bracket of claim 1, wherein the projection extends into the recess and contacts the discrete free-floating spring when the ligating member is moved from the open to the closed position.

3. The orthodontic bracket of claim 1, wherein the discrete free-floating spring is annular, discoidal, oval, helical, round or curved in shape.

4. The orthodontic bracket of claim 1, wherein the recess limits the movement of the discrete spring when the ligating member is moved from the open position to the closed position.

5. The orthodontic bracket of claim 1, wherein the first edge is concentric with a portion of the discrete spring and the second edge is parallel with the path of travel of the projection from the open position to the closed position.

6. The orthodontic bracket of claim 1, wherein a depth of the recess is greater than a thickness of the discrete free-floating spring.

* * * * *